United States Patent [19]

Ciaperoni et al.

[11] 4,126,646

[45] Nov. 21, 1978

[54] THERMOSTABLE FLAMEPROOFING AGENT FOR COPOLYESTERS, PROCESS FOR MAKING IT, COPOLYESTER COMPOSITIONS PREPARED BY USING IT, PROCESS FOR SAID COMPOSITIONS, AND FORMED BODIES MADE FROM SAID COMPOSITIONS

[75] Inventors: Aldemaro Ciaperoni, Bollate; Giuseppe Quaglia, S. Giorgio su Legnano; Gino Dall'Asta, Milan, all of Italy

[73] Assignee: SNIA VISCOSA Societa Nazionale Industria Applicazioni Viscosa S.p.A., Italy

[21] Appl. No.: 732,957

[22] Filed: Oct. 15, 1976

[30] Foreign Application Priority Data

Oct. 20, 1975 [IT] Italy ................. 28435 A/75

[51] Int. Cl.$^2$ .................. C08G 63/66; C08G 63/68
[52] U.S. Cl. .................. 260/860; 260/DIG. 24; 528/191
[58] Field of Search ........ 260/860, 49, 47 C, DIG. 24

[56] References Cited

U.S. PATENT DOCUMENTS

| | | | |
|---|---|---|---|
| 3,234,167 | 2/1966 | Sweeny | 260/30.4 |
| 3,624,034 | 11/1971 | Price et al. | 260/49 |
| 3,663,508 | 5/1972 | Mobius et al. | 260/49 |
| 3,704,279 | 11/1972 | Ismail | 260/61 |
| 3,794,617 | 2/1974 | Mains et al. | 260/47 C |
| 3,867,336 | 2/1975 | Fox | 260/45.7 R |

*Primary Examiner*—Lester L. Lee
*Attorney, Agent, or Firm*—McGlew and Tuttle

[57] ABSTRACT

A thermostable flameproofing agent for copolyesters is prepared by reacting one mol of a diester of an alkali dicarboxyaryl sulphonate with 1–2 mols of at least one tetrabrominated diol in the presence of a transesterification catalyst chosen in the group consisting of compounds of Zn, Co, Ca, Sn, Ti and Mn. Copolyester compositions adapted for the preparation of formed bodies are prepared by the polycondensation of a dicarboxylic arylic acid or its diesters and a saturated aliphatic diol with said flameproofing agent and up to 1% by weight of a derivative of phosphorus in the presence of a catalyst consisting of $Sb_2O_3$ or $GeO_2$. Said compositions preferably have an intrinsic viscosity not less than 0.40 dl/g before their transformation into formed bodies and not less than 0.35 dl/g after said transformation.

18 Claims, No Drawings

THERMOSTABLE FLAMEPROOFING AGENT FOR COPOLYESTERS, PROCESS FOR MAKING IT, COPOLYESTER COMPOSITIONS PREPARED BY USING IT, PROCESS FOR SAID COMPOSITIONS, AND FORMED BODIES MADE FROM SAID COMPOSITIONS

BACKGROUND OF THE INVENTION (a) The Field of the invention

This invention refers in general to a thermostable flameproofing agent for polyester compositions suitable for the production of formed bodies, in particular fibers, to a process for its preparation and to a technique for the production of said formed bodies having properties of resistance to the propagation of the flame.

More particularly this invention refers to a product suitable for use as thermostable flameproofing agent for bodies formed from polyester compositions, essentially on a polyethyleneterephathalate and/or polybutyleneterephthalate basis.

(b) The prior art

Methods for the production of formed bodies, in particular fibres, from copolyesters resistant to the propagation of the flame are known in the art.

Two general methods are known to confer to said formed bodies properties of resistance to the propagation of the flame: specifically one of them involves incorporating flameproofing additives in the polyester compositions before the extrusion, while the other involves applying said additives as finishes to the already formed bodies.

With regard to the textile industry, it is much preferable to make fibers from spinnable copolyester compositions which contain flameproofing additives and/or combinations thereof than to apply flameproofing finishes to the fibers and the textile articles.

This latter method is disadvantageous because the flameproofing finish has a short life and is progressively removed in the course of the use and the washings of the textile article, as is well known in the art. Therefore the more recent art is oriented to the preparation of polyester compositions already comprising flameproofing agents, for the production of flameproofed formed bodies, in particular textile articles.

SUMMARY OF THE INVENTION

The Applicant has now surprisingly found a new thermostable flame-proofing agent for polyesters, containing besides bromine atoms (which notoriously confer flame-retardant properties) also atoms of sulphur which surprisingly enhance said properties, the concurrent presence of both elements having a synergic effect.

The flame-proofing agent which forms one of the objects of this invention is characterized by the fact that it is constituted by the product (hereinafter also briefly designated as "α") of the reaction of 1 mol of a diester of an alkali dicarboxyaryl-sulphonate (1) with 1-2 mols of at least one tetrabrominated diol having the general formula (2)

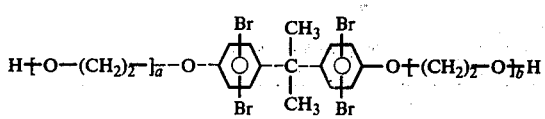

wherein $a$ and $b$ represent, the one independently of the other, a whole number from 1 to 3 inclusive, said reaction being effected in the presence of a transesterification catalyst chosen in the group consisting of compound of Zn, Co, Ca, Sn, the compounds of Ti and Mn being preferred. Said reaction is effected at a temperature comprised between 240° and 280° C preferably in the absence of a solvent. Preferably compound (1) is a compound having the general formula (1a):

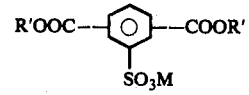

wherein R' represents an alkyl radical containing from 1 to 3 carbon atoms and M represents an atom of Na or K.

More preferably in the compound having the formula (1a), M is Na and R' is $CH_3$.

In the compound of formula (2), $a$ and $b$ are preferably 1. The use of the reaction product (α) as flameproofing agent imparts to the polyester materials, besides improved self-estinguishing properties, a considerable thermostability with a substantial improvement of the resistance to the flame. The polyester fibers obtained from such materials are posessed of a high resistance to the propagation of the flame as shown by the results of the vertical test UNI 5420-64.

It is another object of this invention to provide a process for making a copolyester composition adapted to the production of formed bodies, in particular fibers, having a high thermostability and resistance to the propagation of the flame.

This process is characterized by the polycondensation — in the presence of a conventional catalyst, such as a compound of a polyvalent metal, for instance antimonium oxide, titanium oxide, germanium oxide, zinc oxide etc — of the following components:

(A) a dicarboxylic arylic acid or its methyl diester;
(B) a saturated aliphatic diol;
(C) the reaction product (α);
(D) up to 1% by weight of a phosphorous derivative, as complexing agent.

Preferably the dicarboxylic arylic acid is terephthalic acid, optionally in the form of its diester, and the saturated aliphatic diol is a compound having the general formula (3)

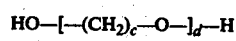

wherein $c$ represents a whole number from 2 to 4 inclusive, and $d$ represents a whole number from 1 to 3 inclusive.

Preferably in the compound having the formula (3) $c$ is 2 and $d$ is 1.

According to the invention the components hereinbefore indicated by (A), (B), (C) are copolymerized in the presence of (D) and of a catalyst, for example chosen among $Sb_2O_3$ and $GeO_2$, under condition conventional for this type of copolymerization, until a stable viscosity is reached, signifying that the polycondensation has been substantially completed, and then the reaction is stopped before the intrinsic viscosity of the resulting composition decreases below a value acceptable for its successive extrusion, for example below 0.40 dl/g (measured in 60/40 by weight mixture phenol/tetrachloroethane at 20° C). The preferred embodiment of the process for making the copolyester composition adapted for the production of fibers according to the invention, comprises the polycondensation of one mol of the dimethylester of terephthalic acid, from 1 to 2.5 mols of ethylene glycol and from 0.005 to 0.5 mols of the product (α) of the reaction of the sulphonated derivative (1) with the brominated derivative (2).

The catalysts employed for the polycondensation and their transformation products as well as those employed for the preparation of the reaction product (α) are present in the amounts that are conventional for this type of reactions.

A further object of this invention is the copolyester composition adapted to the production of formed bodies, in particular fibers, having thermostability and resistance to the propagation of the flame, containing as flame-proofing agent the reaction product (α) hereinbefore defined.

Said composition possesses an intrinsic viscosity (measured as hereinbefore stated): in the form of powder or chips or particles, or any form that is not the final one of formed bodies, in particular filaments or fibers, not lower than 0.4 dl/g, preferably not lower than 0.55 dl/g; when in the final form of formed bodies, in particular filaments or fibers, not lower than 0.35 dl/g, preferably not lower than 0.40 dl/g.

The bromine and sulphur content, in the copolyester according to the invention, may be from 2 to 15% by weight Br and from 0.1 to 1% by weight S. The phosphorous derivatives present do not exceed 1% by weight of the composition.

The formed bodies, in particular the fibers, filaments and textile manufacts, containing as flame-proofing agent the reaction products (α) are a further object of this invention.

Another advantage of this invention deriving from the use of the reaction product (α) is constituted by the possibility of dying the flame-resistant copolyester with basic dyes which is not possible with normal polyesters, e.g. of the polyethyleneterephthalate type.

The intrinsic viscosity, which in the following examples is indicated by the symbol [η] and is expressed in dl/g, is measured at 20° C after dissolving the polyester in a mixture of phenol and tetrachloroethane in weight ratios 60 to 40.

PREFERRED EMBODIMENTS OF THE INVENTION

EXAMPLE 1: Preparation of an ester from 2,2-bis-3,3-dibromo-4(2-hydroxyethoxy)phenyl-propane with 1-sulpho-benzene-3,5-dicarboxyl ester.

In an autoclave provided with a stirrer, having the capacity of 30 l at 150°, there are introduced in a nitrogen stream 7.67 Kg of 2,2-bis-3,3-dibromo-4(2-hydroxyethoxy)phenyl-propane, 1,8 Kg of 1-sulphobenzene-3,5-dicarboxyl dimethylester (molar ratio 2:1) and 10.6 of Ti tetrabutoxide. A nitrogen environment is established within the autoclave. The whole is heated under stirring until a temperature of 230°-240° C is reached, at which temperature the transesterification occurs with the evolution of the amount of methanol (cm$^3$ 425) corresponding to a yield of 88.5%. 125 g of $NaH_2PO_1 \cdot H_2O$ are added, the stirring is continued for another 30', then the molten product having a yellow colour is discharged, is cooled and the same is ground.

EXAMPLE 2: Preparation of a copolyester having properties of resistance to the flame by the use of the product obtained in Example 1.

In an autoclave having the capacity of 30 l, provided with a stirrer there are introduced, at 150° C, 8.0 Kg of dimethylterephthalate, 5.35 Kg of ethylene glycol, 1.045 Kg of the reaction product prepared according to Example 1, 3.92 g of manganese acetate and 82.2 g of titanium dioxide.

The whole is heated under nitrogen at 180°-220° C for 160' until the distillation of methanol ceases. The reaction mixture is transferred into a second autoclave, also provided with a stirrer, and 3.2 g of antimonium trioxide and 1.63 g of phosphorous acid are introduced in a nitrogen stream. The whole is heated to 270° C under a vacuum and the autoclave is discharged after 4-5 hours of vacuum.

The polymer has the following characteristics:

| | |
|---|---|
| - [η] | 0.55 dl/g |
| - Br content | 5% by weight |
| - S content | 0.27 by weight |
| - terminal carboxyl groups | 48 equiv/ton |
| - melting temperature | 237° C |
| - decomposition temperature | 343° C (measured by thermogravimetric analysis.) |

25 Kg of the copolyester obtained are spun by melting and extruding under the conditions normally used for spinning polyethyleneterephthalate at a yarn take up speed of 680 m/min. The yarn is drawn at a temperature of 107° to a draw ratio 1:4.06. The drawing takes place regularly.

The characteristics of drawn yarn are elongation at break 17%, tenacity 3.62 g/den. A stocking having a weight of 90-100 g/m$^2$ is made from it; 15 × 7.5 cm test samples are prepared from the stocking and are subjected to the inflammability test UNI 5420-64. By this test the flame propagation time, which is the time within the flame becomes estinguished after the igniting flame has been removed, and the length of the burnt sample after a contact of 4 seconds with the igniting flame, are measured.

The results of the test are listed in Table 1.

TABLE 1

| | | Average of 5 test samples |
|---|---|---|
| Conventional polyethyleneterephthalate, titer 150/32 den/filament (weight 100 g/m$^2$) | Flame propagation time (sec) | 12.5 |
| | Burnt length (cm) | 11 |

| | | Average of 10 test samples |
|---|---|---|
| Copolyester prepared according to Example 2, same, titer (weight 95 g/m$^2$ | Flame propagation time (sec) | 1 |
| | Burnt length (cm) | 7 |

As it is seen from the table, the copolyester obtained according to Example 1 has a higher resistance to the propagation of the flame.

EXAMPLE 3: Reaction of the dimethylester of sulphoisophthalic acid (1) and the brominated derivative (2) in the presence of a catalyst different from that employed in Example 1.

In a vessel provided with a stirrer there are charged in a nitrogen environment, 248.5 g of 1-sulpho-3,5-benzene-dicarboxyl dimethylester and 1060 g of 2,2-bis-3,3-dibromo-4(2-hydroxyethoxy)phenyl-propane with 6.66 g of manganese acetate (6000 parts per million by weight with respect to the brominated derivative).

After 1 h and 35' at 240°, 48 cm³ of methyl alcohol are distilled with a yield of 68.2% of the desired reaction product.

The product, after cooling, is ground and used in a polycondensation test to obtain flame retarded copolyester.

EXAMPLE 4: Preparation of a copolyester having properties of resistance to the flame, by the use of the product obtained according to Example 3.

In the autoclave described for Example 2, the following products are charged: 8.0 Kg of dimethylterephtalate, 5.35 Kg of ethylene glycol, 1.045 Kg of the product obtained according to Example 3 and 82 g of titanium dioxide(in a dispersion in ethylene glycol at 39% concentration). The operations of Example 2 are repeated, the transesterification is complete after 3 hours and 20' at 180°-220° C.

The mixture obtained by transesterification is then transferred into a second autoclave, then 4.0 g of monosodium fosfate and 3.2 g of antimonium trioxide are introduced in a nitrogen stream. The whole is heated at 270° C under a Vacuum. After 5 hours and 30' the polymer is discharged from the autoclave; it possesses the following characteristics: $[\eta]=0.54$ dl/g; terminal carboxyl groups: 40 equiv/ton. The fibers produced from this composition have the same flame-proofing properties as those of the composition of Example 2.

The foregoing examples are illustrative and not limitative and the invention may be carried into practice with all such modifications as are within the capabilities of persons skilled in the art.

The embodiments of the invention described in the examples are considered to be among the most preferred ones because the raw materials are easily available and have a low cost, because their processing is well known, etc., but the invention has been succesfully carried into practice in other ways, e.g. by using propylene glycol or butylene glycol as the aliphatic diol (component B).

We claim:

1. Thermostable flame-proofing agent for copolyester compositions, adapted to the production of fibers, which comprises a product ($\alpha$) of the reaction of 1 mole of (1) a dialkyl diester of an alkali dicarboxyaryl-sulphonate, said dialkyl having not more than three carbon atoms in each alkyl group, with (2) from 1 to 2 moles of at least a tetrabrominated diol having the general formula

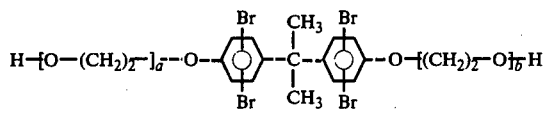

wherein $a$ and $b$ represent, independently, one of the other, a whole number from 1 to 3 inclusive, said reaction being effected in the presence of a transesterification catalyst selected from the group consisting of compounds of Zn, Co, Ca, Sn, Ti and Mn.

2. Flame proofing agent according to claim 1, characterized by the fact that said diester is a compound having the general formula

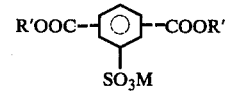

wherein R' represents an alkyl radical containing from 1 to 3 carbon atoms and M represents an atom of Na or K.

3. Flame-proofing agent according to claim 2, wherein R' is $CH_3$ and M is Na.

4. Flame-proofing agent according to claim 1, wherein the values of a and b in said diol are 1 each.

5. Composition for the production of formed bodies having high thermostability and resistance to the propagation of a flame, which comprises a copolyester and, as a flame-proofing agent, the units of the reaction product ($\alpha$) which is defined as the product ($\alpha$) of the reaction of 1 mole of a dialkyl diester of an alkali dicarboxyaryl-sulphonate, said dialkyl having not more than three carbon atoms in each alkyl group, (1) with 1–2 mol of at least a tetrabrominated diol having the general formula:

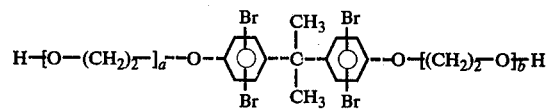

wherein $a$ and $b$ represent, independently one of the other, a whole number from 1 to 3 inclusive, said reaction being effected in the presence of a transesterification catalyst selected from the group consisting of compounds of Zn, Co, Ca, Sn, Ti and Mn.

6. Composition according to claim 5, characterized by the fact that the copolyester, in the condition of a powder or chips or particles, before its transformation into a formed object, has intrinsic viscosity not less than 0.40 dl/g (measured in a 60/40 by weight mixture phenol-tetrachloroethane at 20° C).

7. Composition according to claim 6, characterized by the fact that the said viscosity is not less than 0.45 dl/g.

8. Composition according to claim 5, characterized by the fact that the copolyester, in the usable formed state, has an intrinsic viscosity not less than 0.35 dl/g (measured as in claim 6).

9. Composition according to claim 7, characterized by the fact that the said viscosity is not less than 0.40 dl/g.

10. As new industrial products, textile fibers and filaments having high mechanical characteristics, a high thermostability and a substantial resistance to the propagation of flame, consisting of a copolyester composition according to claim 5.

11. Process for obtaining a copolyester composition adapted to the production of formed bodies having a high thermostability and resistance to the propagation of flame, characterized by the polycondensation, in the presence of a conventional catalyst, of the following components:

(A) a dicarboxylic arylic acid or its diester;

(B) a saturated aliphatic diol;
(C) the reaction product (α) according to claim 41; and
(D) up to 1% by weight of an acid derivative of phosphorus (III or V) or a salt thereof.

12. Process according to claim 11, characterized by the fact that the copolycondensation of components (A), (B), and (C), is effected in the presence of (D) and of a catalyst selected from the group consisting of $Sb_2O_3$ and $GeO_2$, until a stable viscosity is reached, evidencing the substantial completion of the polycondensation, and by the subsequent stopping of the reaction before the intrinsic viscosity of the said resulting composition decreases below a value acceptable for successive extrusion.

13. Process according to claim 11, wherein the saturated aliphatic diol is a compound having the general formula $$HO-[-(CH_2)_c-O-]_d-H \qquad (3)$$

wherein $c$ represents a whole number from 2 to 4 inclusive, and $d$ represents a whole number from 1 to 3 inclusive.

14. Process according to claim 13, characterized by the fact that in the compound having formula (3), $d$ is 1.

15. Process according to claim 14, characterized by the fact that in the compound having formula (2) $c$ is 2.

16. Process according to claim 15, characterized by the fact that one mole of terephtalic acid dimethylester is copolymerized with 1 to 2.5 mols of ethylene glycol and with from 0.005 to 0.15 mols of the reaction product (α).

17. Process according to claim 15, characterized in that the polycondensation is discontinued when the power absorbed by a stirrer acting on the polycondensate has been stable.

18. Process according to claim 17, characterized by the fact that the said viscosity is not less than 0.40 dl/g.

* * * * *